United States Patent
McCabe et al.

(10) Patent No.: US 10,286,048 B2
(45) Date of Patent: May 14, 2019

(54) POLYVALENT VENOM VACCINES

(71) Applicants: James G. McCabe, Thousand Oaks, CA (US); James Brockett, Thousand Oaks, CA (US); Thomas M. McCabe, Thousand Oaks, CA (US)

(72) Inventors: James G. McCabe, Thousand Oaks, CA (US); James Brockett, Thousand Oaks, CA (US); Thomas M. McCabe, Thousand Oaks, CA (US)

(*) Notice: Subject to any disclaimer, the term of this patent is extended or adjusted under 35 U.S.C. 154(b) by 0 days.

(21) Appl. No.: 16/048,193

(22) Filed: Jul. 27, 2018

(65) Prior Publication Data

US 2019/0030142 A1   Jan. 31, 2019

Related U.S. Application Data

(60) Provisional application No. 62/538,126, filed on Jul. 28, 2017.

(51) Int. Cl.
*A61K 39/00* (2006.01)

(52) U.S. Cl.
CPC .... *A61K 39/0005* (2013.01); *A61K 2039/545* (2013.01); *A61K 2039/552* (2013.01); *A61K 2039/55505* (2013.01); *A61K 2039/575* (2013.01); *A61K 2039/70* (2013.01)

(58) Field of Classification Search
CPC ......... A61P 31/00; C07K 16/02; C07K 16/06; C07K 16/12; C07K 16/18; C07K 17/08; A61K 38/00; A61K 39/00
USPC ......... 424/542; 435/174, 180; 436/518, 529; 530/413, 810, 813
See application file for complete search history.

(56) References Cited

U.S. PATENT DOCUMENTS

| | | | |
|---|---|---|---|
| 5,196,193 A * | 3/1993 | Carroll | C07K 16/02 |
| | | | 424/172.1 |
| 5,443,976 A | 8/1995 | Carroll | |
| 5,536,496 A * | 7/1996 | Frantz | A61K 39/102 |
| | | | 424/184.1 |

OTHER PUBLICATIONS

Cates et al., (AJVR. vol. 76, No. 3. Mar. 2015; pp. 272-279) (Year: 2015).*
Rogero et al., (J. Venom Anim. Toxins vol. 1 N.1 Botucatu 1995).*
Grasset et al. British journal of experimental pathology. Oct. 1933. Issue 14, vol. 5, pp. 308-317.
PCT Written Opinion.
Cates et al., American Journal of Veterinary Research. Mar. 2015. vol. 76, issue 3, pp. 272-279.
Leonard et al., Veterinary Medicine: Research and Reports. Oct. 31, 2014, vol. 2014, pp. 153-158.
PCT Search Report.

* cited by examiner

*Primary Examiner* — Jana A Hines
(74) *Attorney, Agent, or Firm* — Eric P. Mirabel

(57) ABSTRACT

This disclosure relates to materials and methods useful for vaccinating mammals against the effects of envenomation by venomous organisms (including the Western Rattlesnake) by making use of venom from multiple distinct populations, subspecies or species of the organism, to make a vaccine more broadly protective against other populations, subspecies or species. This disclosure also relates to a method for determining which organisms which are capable of envenomation should be pooled for optimizing the coverage and efficacy of a vaccine which is produced from the venoms (or toxoid derivatives) in the combination.

8 Claims, No Drawings

POLYVALENT VENOM VACCINES

TECHNICAL FIELD

This invention relates to the use of toxoid snake venom or other toxoid venoms for vaccinating mammals against the effects of envenomation by multiple species of venomous snakes or other animals, by using toxoids derived from snakes or animals sourced from multiple geographical locations; and to determination of which toxoids should be pooled for optimizing the coverage of the resulting vaccine.

BACKGROUND

A wide variety of organisms (including certain species of snakes; spiders, scorpions and other arachnids; insects; fish; jellyfish; and lizards) are capable of producing venoms, and of transmitting them ("envenomation") by either biting or stinging.

Rattlesnake venom is a complex mixture of toxic components (individually referred to as toxins), composed mainly of both enzyme and non-enzyme proteins. Toxins are divided into more than twenty different protein families that are defined by their molecular structure. While families of toxins share a general structure, there may be a variety of toxic activities represented by a single toxin family. Typically, an individual rattlesnake's venom will contain toxins representing a dozen toxin families and can contain upwards of 50 unique toxins. While lethality is a major concern in envenomation, other serious adverse events which are likely, include hemorrhage, tissue necrosis and systemic blood clotting, among others.

A vast majority of snakebite envenomation cases in the state of California result from encounters with individuals from the two subspecies of Western Rattlesnake, the Northern Pacific Rattlesnake (*Crotalus oreganus oreganus*) and the Southern Pacific Rattlesnake (*Crotalus oreganus helleri*). The venom of this species can cause a wide range of clinical issues, including tissue damage, blood clotting and effects on the nervous system.

One method of acutely treating domestic animals or humans that have been envenomated by venomous snakes or other venomous organisms is to administer an intravenous dose of monoclonal or polyclonal antibodies harvested from a mammalian species (e.g. sheep, horse, or goat) that has been immunized against a venom. Antibody-based therapeutics are known as antivenoms or antivenins.

Snake antivenom is "monovalent" if it is produced from the venom of a single species of snake and "polyvalent" if produced from the venom of multiple species of snakes.

While the use of antivenom is an acute treatment option used following an envenomation event, vaccination against venom is a prophylactic—for protecting an animal or human before they suffer envenomation. All toxins can be denatured by physical or chemical means to produce attenuated materials known as toxoids, which immunologically resemble the source toxin and can produce a protective immune response. While toxoids closely resemble the original toxins in their structure, the neutralization process(es) disrupt enough molecular structure to render the toxoids nontoxic.

The vaccination of a mammal against the effects of envenomation can be accomplished using either bioactive venom toxins or venom toxoids. Toxoids are preferred to minimize the risk of injury or death to the mammal from toxin. Toxoids are preferably administered at a dose and frequency to generate a strong and lasting immune response. Thus in designing a toxoid vaccine, the goal is to present the patient's immune system with enough toxoids to stimulate the immune system to defend against each of the potentially dangerous components (or its immunological equivalent) that might be transmitted in envenomation.

Snake venom is known to vary within and between species. There are more than 30 distinct species of venomous snakes in the contiguous U.S., each with a distinct venom composition compared with other species and some with distinct compositions between subspecies. Existing research also shows that snake venom varies within and between geographic populations of venomous snake. This immense amount of variation is thought to arise from locality specific evolutionary pressures acting on snake venom composition and affecting the ecological fitness of a population over time.

The Southern Pacific Rattlesnake (*Crotalus oreganus helleri*) ranges across some of the most heavily populated areas of Southern California. A number of geographically separate populations of the Southern Pacific Rattlesnake exhibit significant variations in venom composition, each with unique biochemical properties. The Northern Pacific Rattlesnake (*Crotalus oreganus oreganus*) ranges further north, and shows local variations in venom composition.

There is only one commercially-available snake venom vaccine (Canine and Equine Rattlesnake Toxoid Vaccine, from Red Rock Biologics, Woodland, Calif.) approved by the USDA-CVB for use in domesticated animals (dogs and horses). The vaccine is monovalent and is produced from a single species—the Western Diamondback Rattlesnake (*Crotalus atrox*). This product is referred to as "CAT Vaccine" (*Crotalus atrox* toxoid vaccine).

The CAT vaccine is a sub-lethal dose of a mixture of toxoids that causes the vaccinated mammal to mount an immune response and produce its own anti-venom antibodies against future snakebite. Antibodies produced by an animal immunized with the CAT vaccine have limited or no ability to protect against the venom of species of rattlesnake other than the Western Diamondback Rattlesnake (*Crotalus atrox*). See Cates et al. (2015), *Comparison of the protective effect of a commercially available Western Diamondback Rattlesnake toxoid vaccine for dogs against envenomation of mice with Western Diamondback Rattlesnake (Crotalus atrox), Northern Pacific Rattlesnake (Crotalus oreganus oreganus), and Southern Pacific Rattlesnake (Crotalus oreganus helleri) venom*, Am. J. Vet. Res. 76(3):272-9.

The failure of this CAT Vaccine to protect mice, an experimental model mammal, when experimentally envenomated with the venom from a Southern Pacific Rattlesnake (*Crotalus oreganus helleri*) presumably results from differences between the venom used to formulate the CAT vaccine and the venom of the Southern Pacific Rattlesnake.

The derived heterodimeric lectin toxins (α- and β-chains) characteristic of viper venoms, which exhibit a diversity of biological activities including anticoagulation and agonism/antagonism of platelet activation or procoagulation, are both absent from the San Jacinto Mountain population, but are present in all other populations of the Southern Pacific Rattlesnake. The extreme variation of venom composition between the different populations of Southern Pacific Rattlesnake and the absence of the neurotoxin phospholipase A2 complex in the CAT vaccine renders the CAT vaccine ineffective against not only all of the Southern Pacific Rattlesnake populations, including the San Jacinto Mountain population, but also against envenomation from other species of rattlesnake including the Mojave Rattlesnake (*Crotalus scutulatus*).

Thus, there is currently a great need for polyvalent and broadly protective venom toxoid vaccines in the regions where dangerous snakes reside. A broadly protective vaccine is expected to significantly reduce mortality of dogs and horses from snakebite envenomation, significantly reduce the suffering of canine and equine patients and their owners, and significantly reduce the financial burden to dog and horse owners by reducing the duration of treatment and hospitalization of envenomated animals.

SUMMARY

The preferred embodiment relates to: a polyvalent vaccine that includes toxoids derived from the venom of multiple rattlesnake species or sourced from rattlesnakes from distinct geographical regions, which will protect a mammal from envenomation by such species in addition to subspecies and other species. The desired vaccine will protect against rattlesnakes indigenous to a particular geographical region, and preferably, subspecies and other species of rattlesnakes, and more preferably, all species of rattlesnakes and some other species of venomous snake.

The invention also relates to a polyvalent vaccine with toxoids derived from the venom of a variety of snakes and scorpions native to the Middle East, including the yellow scorpion (*Leiurus quinquestriatus*), fat-tailed scorpions such as the black scorpion (*Androctonus crassicauda*) and *A. amoreuxi*, as well as *Buthus arenicola, B. mimax, B. occitanus, L. quinquestriatus hebreus*, and the Arabian cobra (*Naja hale arabicus*), the black desert cobra (*Walterinesia aegyptia*), *Bitis arietans, Echis colorants, E. carinantus*, and *Verastes cerastes*, These venoms can be denatured, mixed and prepared as a broadly-protective vaccine against envenomation by these organisms, and related species, using the technology, methodologies, methods, processes and practices described herein.

The invention also relates to a polyvalent viral vaccine for mosquito-borne viruses including the West Nile virus, chikungunya virus, the four common variants of dengue virus, and the Zika virus. These viruses can be denatured and prepared as a broadly-protective vaccine against several mosquito-borne viruses, using the technology, methodologies, methods, processes and practices described herein.

A preferred embodiment also relates to venom combinations from populations of Western rattlesnakes (*Crotalus oreganus*) so that venom combinations from these distinct populations will include all dangerous components (or their immunological equivalent) to which a mammal could be exposed upon envenomation, and then using this combined venom to produce more effective toxoid rattlesnake vaccines for at-risk mammals in the relevant range of such species. The vaccine would preferably be protective against all subspecies of Western rattlesnake, including the Southern Pacific Rattlesnake and the Northern Pacific Rattlesnake, and will preferably also provide some degree of cross protection against envenomation by any pit viper in the United States, including the Mojave Rattlesnake (*Crotalus scutulatus*), all subspecies of the Prairie Rattlesnake (*Crotalus viridis* ssp.), Eastern Diamondback Rattlesnake (*Crotalus adainanteus*), Western Diamondback Rattlesnake (*Crotalus atrox*), Red Diamondback Rattlesnake (*Crotalus ruher* ssp.), Timber Rattlesnake (*Crotalus horridus*), Massasauga (*Sistrurus* ssp.), Sidewinder (*Crotalus cerastes*), water moccasins (*Agkistrodon* sp.), and copperheads (*Agkistrodon* sp.).

The venom combinations can be treated to make toxoids by any of a number of methods well-known to those skilled in the art, and then stored for administration by: simply refrigerating or freezing a liquid venom mixture, lyophilizing such liquid mixture, adding alum or one or more other adjuvant materials to such liquid mixture and storing it refrigerated or frozen or lyophilizing the mixture, or by any other such well-known method for preserving toxoid vaccines, including adding preservatives e.g., thimerosal. To optimally preserve the activity of enzymes in the formulation, preferred storage conditions are at −20° C. to −70° C., and can include stabilizers such as glycerol that have low freezing points and low vapor pressures. The formulation for administration may further include buffers and salts, and/or other well-known formulation materials, all of which are well-known and require little or no experimentation to optimize in a formulation.

The toxoid can also first be created from each venom type in the combination, and then the separate toxoid types can be mixed to form a toxoid combination, which is then mixed with alum or adjuvants if desired, and stored under appropriate conditions to preserve it.

The present invention also includes the process of mapping the geographical distribution of any venom, toxin, poison, or other dangerous material generated by plants or animals, and then constructing a polyvalent vaccine against this combination of venoms, toxins, poisons, or other dangerous materials so as to provide improved protection for a mammalian subject which is at risk of encountering any of the toxins, poisons, or other dangerous materials.

These, as well as other materials, components, steps, features, objects, benefits, and advantages, will now become clear from a review of the following detailed description.

DETAILED DESCRIPTION

The method of generating and dosing a mammal with Western Rattlesnake toxoid vaccine is illustrated further by the following additional Example 1, and examples of other toxoid vaccines follow. The examples are not to be construed as limiting the disclosure in any way to the specific procedures or products described in them, or in any way other than as stated in the claims.

The goal in dosing is to expose the subject to all antigens needed to stimulate the animal's immune system to defend against rattlesnake and/or other snake venom. A number of well-known formulations and administration protocols can be used to accomplish this, including intraperitoneal, intravenous, intramuscular, or subcutaneous injection. Any other administration method which can meet the goal stated above can also be used.

In addition to adjuvants, stabilizers, buffers and salts, the formulation can include any "pharmaceutically acceptable carrier" including, by way of non-limiting example, a pharmaceutically acceptable solvent, suspending agent, or any other pharmacologically inert vehicle for delivering active toxoids to a subject. Pharmaceutically acceptable carriers can be liquid, and can be selected with the planned manner of administration in mind so as to provide for the desired bulk, consistency, and other pertinent transport and chemical properties. Examples of pharmaceutically acceptable carriers include, without limitation, water; saline solution; fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Example 1. ELISA Protocol of Experiments Demonstrating Protection Against Several Venom Types with a Polyvalent Vaccine Vaccine Formulation: one milliliter (mL) of vaccine contains venom from the Western Rattlesnake (*Crotalus oreganus*) in the quantities and where the donor snakes were from the regions indicated:
- 0.493 mg of venom from donors from the Southern Sierra Nevada Mountains, Calif.;
- 0.493 mg of venom from donors from the Transverse Mountains, Calif.;
- 0.014 mg of venom from donors from the San Jacinto Mountains, Calif.;
- 1:4 Aluminum Hydroxide (Alhydrogel®, InvivoGen); and
- 0.001-0.01% Thimerosal (U.S. Pharmacopeia, 2004).

To determine whether the vaccine could elicit an immune response in a mouse model, and show broad protection, an ELISA was conducted and included, as control, a comparison of the specific immunity of vaccinated mice with those immunized using adjuvant alone. To demonstrate broad protection, specific immunity was determined for individual mice against venoms from rattlesnakes from eight regions, collectively representing six species and subspecies; that is: two populations of Northern Pacific Rattlesnake (*Crotalus oreganus oreganus*; captured from Napa Valley to Sacramento, Calif.; and New Cuyama to Tehachapi, Calif.); two populations of Southern Pacific Rattlesnake (*Crotalus oreganus helleri*; captured from Southern California from Santa Barbara south, and San Jacinto Mountain Range); Western Diamondback Rattlesnake (*Crotalus atrox*); Red Diamondback Rattlesnake (*Crotalus rubes*); Southwestern Speckled Rattlesnake (*Crotalus mitchelli pyrrhus*); and Mojave Rattlesnake (*Crotalus scutulatus scutulatus*). A group of 20 mice were immunized with the vaccine and alum as the adjuvant, to generate polyclonal antibodies using a protocol substantially replicated from Cates et al. (2015) but using a new secondary antibody (Santa Cruz Biotechnology, m-IgGκ BP-HRP, sc-516102) instead of the antibody used by Cates et al., which had been discontinued by the manufacturer.

To prepare the plates, 100 micrograms of each of the eight snake venoms was incubated overnight to induce binding to the wells of an individual ELBA plate (one plate for each venom type). After washing and blocking, 50 µl of mouse serum (diluted 1:8000) was added to the wells. One plate was used in each run in triplicate, with serum from each of the twenty mice in individual wells, and with control serum from mice immunized with adjuvant only (and other controls were assay reagents as well) in the same run. Then the assay process was repeated with another venom until all eight venom types had been completed. This protocol eliminated plate to plate and run to run variations.

Binding was detected using anti-mouse goat antibodies with HRP-activated label, developed at Thermo Scientific Ultra TMB, and the reaction was stopped with sulfuric acid. Developed plates were immediately read at 450 nm. Optical densities measured for each well were averaged and a baseline for detection determined by averaging control wells (12×) for each plate.

To determine whether there was a significant difference in the specific immunity of vaccinated and adjuvant-only control mice, Multiple Response Permutation Procedures (MRPP) with post hoc Indicator Species analysis was performed. This pair of statistical tests is most similar to Multivariate Analysis of Variance (MANOVA) with post hoc tests, and is used to detect statistical differences between known groups and then determine what variables are responsible for determining this difference. MRPP is a non-parametric multivariate procedure that was originally designed for ecological data which violated assumptions of conventional (M)ANOVA, especially the requirement for normally-distributed data. MRPP produces both: (i) a test of significance (p-value) as a criteria for determining whether to reject or fail to reject the null hypothesis that all groups are equal and (ii) a measure of effect size (A-value) known as the chance-corrected within-group agreement (McCune and Grace, 2002). The statistic A describes within-group homogeneity, where A=1 would indicate that all samples are identical within groups. McCune and Mefford (2011) have indicated that A>0.3 is fairly high. Vaccinated mice had significantly higher specific immunity compared to mice inoculated with adjuvant only (MRPP: $p<0.0001$, A=0.48).

Indicator Species Analysis (ISA) was used as a post hoc analysis to MRPP to determine which specific immunities are responsible for driving separation between vaccinated and control mice. The procedure calculates an indicator value (IV) ranging from zero (no indication) to 100 (perfect indication).

Any particular 'species' (in this case an individual snake venom) with perfect indication would allow determination of whether a mouse was from the vaccinated or control group based on the level of specific immunity towards that venom. In addition to the indicator value calculation, a randomization test was conducted to produce a p value to determine whether to reject or fail to reject the null hypothesis that the indicator value is not larger than expected by chance (i.e. that a venom is not a good indicator of treatment group compared to random chance). All eight venoms tested had indicator values with $p<0.001$ and most with strong indication, IV>80: *C. o. oreganus* (Napa/Sacramento), IV=80.5; *C. o. oreganus* (New Cuyama/Tehachapi), IV=81.7; *C. o. helleri* (So. Calif.), IV=85.3; *C. o. helleri* (San Jacinto), IV=71.9; *C. atrox*, IV=84.5; *C. ruber*, IV=87.1; *C. m. pyrrhus*, IV=85.7; *C. s. scutulatus*, IV=67.5. The two venoms that produced the lowest responses, *C. o. helleri* (San Jacinto) and *C. s. scutulatus*, are venoms with an abundance of small myotoxins that may represent moieties that are more difficult for mice to develop an immune response against. However, in both cases vaccinated mice produced detectable quantities of antibodies in a statistically significantly manner; whereas control mice did not have a detectable level of antibodies that were able to bind these venoms.

Example 2: Vaccine Preparation and Administration

Western rattlesnakes selected from three distinct regions (Southern Sierra Nevada Mountains, Calif.; Transverse Mountains, Calif.; San Jacinto Mountains, Calif.) will provide protection against dangerous components of Western Rattlesnake venom throughout its range—which includes a number of western states (Calif., Wash., Oreg., Nev., Ariz., Utah, Id., Wyo., Colo.), and parts of British Columbia and northwestern Mexico. Liquid or lyophilized venom samples from Western Rattlesnakes from these three regions are combined in approximately equal parts, heated or irradiated to denature the dangerous components to produce a toxoid mixture, and mixed with an adjuvant such as alum, stabilizers, buffers, salts, and one or more pharmaceutically acceptable carriers, to produce the final formulation of the polyvalent Western Rattlesnake venom vaccine. A preferred final dosage concentration is one microgram of the active ingredient toxoid per one milliliter dose (i.e., a combination of venom from each of the three California regions above totaling one milligram per one milliliter dose) of denatured venom.

To immunize a less than one hundred pound dog or canine or other mammal, one dose is injected preferably subcutaneously at least once annually, and preferably, at least twice with at least a 30 day interval between doses, before contact between the mammal and rattlesnakes. Ideally, the dosing schedule would be completed before annual warming following the spring equinox in many of the states that have Western Rattlesnake and/or other rattlesnake and venomous snake populations. Some species/geographically distinct populations of rattlesnakes are active year-round in parts of Mexico, California and Arizona so protection of mammals in these locations may require at least bi-annual dosing as protection may fail to extend over the entire rattlesnake active period. Further, dogs over 100 pounds or under 25 pounds may benefit from at least three annual dosings, with the first two doses administered as above and with a third dose administered 30 days after the second dose.

Example 3. Vaccination Against Viruses and Parasites

Published maps of the distribution of the various mosquito vectors in the United States can be combined with the distribution of antigens from several mosquito-borne viruses such as West Nile virus, chikungunya virus, the four common variants of dengue virus, and the Zika virus to determine which components from these viruses will provide all of the dangerous mosquito-borne parasites (like those causing malaria) and viruses likely to be encountered in the U.S. These virus or parasite samples are combined and treated to generate toxoids, and produce a formulation for administration, as in Examples 1 and 2. The formulation is administered as in Example 2.

Example 4. Vaccination Against Other Snakes and Venoms

Published maps of the distribution of a variety of snakes and scorpions native to the Middle East, including the yellow scorpion (*Lentrus quinquestriatus*), fat-tailed scorpions such as the black scorpion (*Andrectonus crassicauda*) and *A. amoreuxi*, as well as *Buthus arenicola, B. mimax, B. occitanus, L. quinquestriatus hebreus*, and the Arabian cobra (*Naja haje arabicus*), the black desert cobra (*Walterinesia aegyptia*), *Bitis arietans, Echis colorants, E. carinatus*, and *Verastes cerastes*, are utilized in combination with data on the characterization of each distinct venom component from these species to determine the minimal set of organisms which will provide complete coverage of every distinct venom component. Liquid venom samples from the identified organisms are combined, treated, formulated and administered as in Examples 1 and 2.

Any combination of features of above process and product is within the scope of the instant disclosure.

The components, steps, features, objects, benefits, and advantages which have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

Unless otherwise stated, all measurements, values, ratings, positions, magnitudes, sizes, and other specifications that are set forth in this specification, including in the exemplary features that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

Relational terms such as "first" and "second" and the like may be used solely to distinguish one entity or action from another, without necessarily requiring or implying any actual relationship or order between them. The terms "comprises," "comprising," "including" and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

The abstract is provided to help the reader quickly ascertain the nature of the technical disclosure. It is submitted with the understanding that it will not be used to interpret or limit the scope. In addition, various features in the foregoing detailed description are grouped together in various embodiments to streamline the disclosure.

| Table of References |
| --- |
| McCune, B., & Grace, J. (2002). Analysis of Ecological Communities. MjM Software, Gleneden Beach, Oregon, U.S.A. |
| McCune, B. & Mefford, M.J. (2011). PC-ORD. Multivariate Analysis of Ecological Data. Version 6.0. MjM Software, Gleneden Beach, Oregon, U.S.A. |
| Cates, C.C., Valore, E.V., Couto, M.A., Lawson, G.W., & McCabe, J.G. "Comparison of the protective effect of a commercially available western diamondback rattlesnake toxoid vaccine for dogs against envenomation of mice with western diamondback rattlesnake (*Crotalus atox*), northern Pacific rattlesnake (*Crotalus oreganus oreganus*), and southern Pacific rattlesnake (*Crotalus oreganus helleri*) venom." *American Journal of Veterinary Research*, 76(3), 272-279 (2015). |

What is claimed is:

1. A polyvalent toxoid vaccine consisting essentially of a combination of denatured venoms from populations of Western Rattlesnakes selected from the Southern Sierra Nevada Mountains, Calif.; the Transverse Mountains, Calif.; and, the San Jacinto Mountains, Calif., which is protective against envenomation from Western rattlesnakes and Mojave, Speckled, Western Diamondback, and Red Diamondback rattlesnakes.

2. The polyvalent toxoid vaccine of claim 1 wherein the vaccine is prepared as a solution.

3. The polyvalent toxoid vaccine of claim 2 wherein the solution has a final concentration of 1 microgram of toxoid per milliliter of solution.

4. The polyvalent toxoid vaccine of claim 1 further including adjuvants, stabilizers, buffers, salts, preservatives and one or more pharmaceutically acceptable carriers.

5. The polyvalent toxoid vaccine of claim 4 wherein the adjuvant is alum.

6. The polyvalent toxoid vaccine of claim 4 wherein the preservative is thimerosal.

7. The polyvalent toxoid vaccine of claim 1 wherein the venoms are denatured by heating.

8. The polyvalent toxoid vaccine of claim 1 wherein the venoms are denatured by irradiation.

* * * * *

UNITED STATES PATENT AND TRADEMARK OFFICE
CERTIFICATE OF CORRECTION

PATENT NO. : 10,286,048 B2
APPLICATION NO. : 16/048193
DATED : May 14, 2019
INVENTOR(S) : J. G. McCabe et al.

Page 1 of 1

It is certified that error appears in the above-identified patent and that said Letters Patent is hereby corrected as shown below:

Column 3, Line 30, change "hale" to -- haje --;
Column 3, Line 60, change "adainanteus" to -- adamanteus --;
Column 3, Line 62, change "ruher" to -- ruber --;
Column 5, Line 33, change "rubes" to -- ruber --;
Column 5, Line 45, change "ELBA" to -- ELISA --;
Column 7, Line 43, change "Lentrus" to -- Leiurus --;
Column 7, Line 62, change "colorants" to -- coloratus --.

Signed and Sealed this
Twenty-fifth Day of June, 2019

Andrei Iancu
*Director of the United States Patent and Trademark Office*